United States Patent [19]

Monnier et al.

[11] Patent Number: 4,724,031
[45] Date of Patent: Feb. 9, 1988

[54] 2,6-DISUBSTITUTED 4-EPOXYPROPYLPHENYL GLYCIDYL ETHERS AND THE USE THEREOF

[75] Inventors: Charles E. Monnier, Villars-sur-Glâne; Sheik Abdul-Cader Zahir, Oberwil; Sameer H. Eldin, Fribourg, all of Switzerland

[73] Assignee: Ciba-Geigy Corporation, Ardsley, N.Y.

[21] Appl. No.: 870,607

[22] Filed: Jun. 4, 1986

[30] Foreign Application Priority Data

Jun. 6, 1985 [CH] Switzerland .................. 2398/85

[51] Int. Cl.[4] ............................. C08G 59/24
[52] U.S. Cl. .................... 156/330; 525/481; 528/87; 528/91; 528/93; 528/94; 528/102; 528/103; 528/104; 528/109; 528/111; 528/112; 528/122; 528/123; 528/124; 549/525; 549/555; 549/559; 156/307.3
[58] Field of Search ............... 528/87, 102, 103, 104, 528/91, 94, 93, 111, 112, 122, 123, 124, 109; 549/555, 559, 525; 525/481; 156/330, 307.3

[56] References Cited

U.S. PATENT DOCUMENTS

| | | |
|---|---|---|
| 2,965,607 | 12/1960 | Martin et al. |
| 2,965,608 | 12/1960 | Martin et al. |
| 3,374,203 | 3/1968 | Schmukler ............... 528/87 |
| 3,773,799 | 11/1973 | Schmid ............... 528/87 X |
| 3,925,315 | 12/1975 | Schmid ............... 528/87 |
| 4,384,129 | 5/1983 | Zahir et al. ............... 528/101 X |

OTHER PUBLICATIONS

Houben-Weyl, Methoden Der Organischen Chemie, pp. 502–507
John D. Roberts & Marjorie C. Caserio, Basic Principles of Organic Chemistry, p. 907 (1965).

Primary Examiner—Earl Nielsen
Attorney, Agent, or Firm—Luther A. R. Hall

[57] ABSTRACT

2,6-Disubstituted 4-epoxypropyl glycidyl ethers of the formula

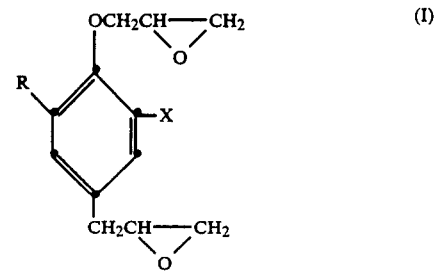

wherein X is a group R' or X is a group of the formula

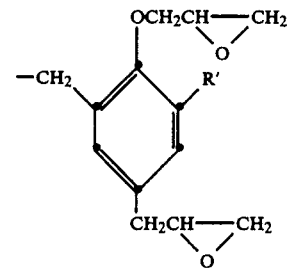

and each of R and R' independently of the other is $C_1$–$C_4$ alkyl, $C_1$–$C_4$ alkoxy, a halogen atom or $C_6$–$C_{10}$ aryl, can be used, together with customary epoxy resin hardeners, for the preparation of cured products, in particular for application in the electronics industry, or as adhesives. Compounds of the formula are also valuable reactive diluents for curable epoxy resin mixtures.

10 Claims, No Drawings

2,6-DISUBSTITUTED 4-EPOXYPROPYLPHENYL GLYCIDYL ETHERS AND THE USE THEREOF

The present invention relates to novel 2,6-disubstituted 4-epoxypropylphenyl glycidyl ethers, to curable mixtures containing such 4-epoxypropylphenyl glycidyl ethers and to the use thereof, e.g. for the preparation of cured products.

Glycidyl ethers of mononuclear or polynuclear phenols containing 2,3-epoxypropyl groups in one or both ortho-positions to the 2,3-epoxypropoxy group are known from the literature (q.v. e.g. British patent specification No. 828 364). Said phenyl glycidyl ethers are prepared by epoxidation of the corresponding o-allylphenols. These o-allylphenols are obtained by Claisen rearrangement of the phenylallyl ethers. However, mixtures of isomers or mixtures of 2-allylphenols and 2,6-diallylphenols are thereby formed.

The present invention relates to novel highly pure 4-(2,3-epoxypropyl)-2,6-disubstituted phenyl glycidyl ethers of the formula

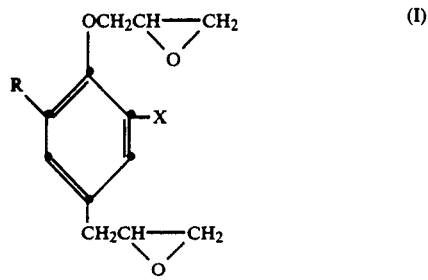

wherein X is a group R' or X is a group of the formula

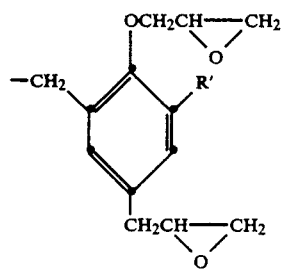

and each of R and R' independently of the other is $C_1-C_4$alkyl, $C_1-C_4$alkoxy,

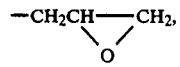

a halogen atom or $C_6-C_{10}$aryl.

Alkyl and alkoxy substituents R and R' may be straight chain or branched. Examples of such groups are: methyl, ethyl, n-propyl, isopropyl, n-butyl, sec-butyl, tert-butyl, methoxy, ethoxy, n-propoxy, n-butoxy and sec-butoxy. Suitable aryl groups R and/or R' are e.g. 1-naphthyl, 2-naphthyl and, in particular, phenyl. R and/or R' as halogen atoms are e.g. bromine or fluorine atoms or, in particular, chlorine atoms.

Preferred compounds of formula I are those wherein each of R and R' independently of the other is $C_1-C_4$alkyl, $C_1-C_2$alkoxy, a halogen atom, in particular a chlorine atom, or phenyl. In accordance with a further preference, R and R' have the same meaning. Particularly preferred compounds of formula I are those wherein n is 1 and each of R and R' is methyl, tert-butyl, methoxy, chlorine or phenyl. The most preferred compounds of formula I are those wherein each of R and R' is methyl.

The compounds of formula I can be prepared in a manner known per se, e.g. by epoxidising an allylphenyl glycidyl ether of formula II

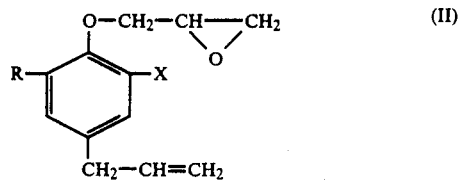

wherein X is as defined for formula I and each of R and R' independently of the other is $C_1-C_4$alkyl, $C_1-C_4$alkoxy, allyl, a halogen atom or $C_6-C_{10}$aryl, in the presence of a peracid.

Suitable peracids are, in particular, organic peracids such as performic acid, peracetic acid, perbenzoic acid and monoperphthalic acid.

The organic peracids can be employed as such or they can be formed in situ, for example from aliphatic or aromatic carboxylic acids, carboxylic acid anhydrides, carboxylates, acid chlorides or ketone and hydrogen peroxide. For the formation of the peracids in situ, it is preferred to use aliphatic or aromatic monocarboxylic or dicarboxylic acids or the anhydrides thereof, e.g. formic acid, acetic acid, propionic acid, succinic anhydride, benzoic acid or phthalic acid, and hydrogen peroxide, optionally with the addition of acid catalysts such as sulfuric acid or alkali metal salts. The epoxidation of the compounds of formula II is preferably carried out in the presence of performic acid or peracetic acid, the acid being either preformed or produced in situ. If desired, inorganic peracids may also be used, e.g. permolybdic acid, pervanadic acid or pertungstic acid. The epoxidising agent (peracid) is conveniently used in an amount of at least 1 mole per allyl group present and is preferably used in excess, e.g. in a 20 to 200% molar excess. Thus if R and/or R' are allyl, then these groups are also epoxidised.

The epoxidation of the compounds of formula II is advantageously carried out in the presence of inert organic solvents, optionally with the addition of buffers such as sodium acetate or sodium hydrogen phosphate. Examples of suitable solvents are unsubstituted or halogenated aliphatic or aromatic hydrocarbons such as chloroform, dichloromethane, benzene, toluene and chlorobenzene, ethers such as diethyl ether, diisopropyl ether, dioxane and tetrahydrofuran, as well as alkyl carboxylates such as ethyl acetate and n-butyl acetate. Preferred solvents are halogenated, in particular chlorinated, aliphatic hydrocarbons, with chloroform being particularly preferred. The epoxidation temperatures are generally in the range from $-10°$ to $+100°$ C., preferably from $+10°$ to $+60°$ C.

The starting materials of formula I are known or they can be prepared by methods known per se by reacting the corresponding 2,6-disubstituted 4-allylphenols with epihalohydrins, in particular, epichlorohydrin, in the presence of catalysts.

The compounds of formula I are highly pure substances which can be distilled and recrystallised and which are free from chloride and alkali metal ions. They are obtained in very high yields.

The compounds of formula I are suitable for the preparation of cured products. Accordingly, the invention also relates to curable mixtures containing (a) a compound of formula I and (b) a hardener for the component (a).

Mixtures of various compounds of formula I and/or hardeners may also be used.

Suitable hardeners (b) are in general any epoxy resin hardeners such as cyanamide, dicyandiamide, polycarboxylic acids, polycarboxylic acid anhydrides, polyamines, polyaminoamides, adducts of amines and polyepoxides and polyols.

Suitable polycarboxylic acids and their anhydrides are e.g. phthalic anhydride, tetrahydrophthalic anhydride, hexahydrophthalic anhydride, methyltetrahydrophthalic anhydride, endomethylenetetrahydrophthalic anhydride, hexachloroendomethylenetetrahydrophthalic anhydride, trimellitic anhydride, pyromellitic anhydride, maleic anhydride, succinic anhydride, nonenylsuccinic anhydride, dodecenylsuccinic anhydride, polysebacic polyanhydride and polyazelaic polyanhydride as well as the acids pertaining to said anhydrides.

Examples of polyamines which are suitable hardeners are aliphatic, cycloaliphatic, aromatic and heterocyclic polyamines such as ethylenediamine, propane-1,2-diamine, propane-1,3-diamine, N,N-diethylethylenediamine, hexamethylenediamine, diethylenetriamine, triethylenetetramine, tetraethylenepentamine, N-(2-hydroxyethyl)-, N-(2-hydroxypropyl)- and N-(2-cyanoethyl)diethylenetriamine, 2,2,4- and 2,4,4-trimethylhexane-1,6-diamine, m-xylylenediamine, N,N-dimethyl- and N,N-diethylpropane-1,3-diamine, bis(4-aminocyclohexyl)methane, 2,2-bis(4-aminocyclohexyl)propane, 2,2-bis(4-amino-3-methylcyclohexyl)propane, 3-aminomethyl-3,5,5-trimethylcyclohexylamine (isophoronediamine), m- and p-phenylenediamine, bis(4-aminophenyl)methane, bis(4-aminophenyl)sulfone, aniline-formaldehyde resins and N-(2-aminoethyl)piperazine. Suitable polyaminoamides are e.g. those which are prepared from aliphatic polyamines and dimerised or trimerised unsaturated fatty acids.

Suitable adducts of amines with polyepoxides are e.g. adducts of aliphatic or cycloaliphatic diamines such as 1,6-hexamethylenediamine, 2,2,4- and 2,4,4-trimethylhexane-1,6-diamine or isophoronediamine with known diglycidyl ethers.

Suitable polyol hardeners (b) are in particular mono- or polynuclear aromatic polyols, including novolaks, such as resorcinol, hydroquinone, 2,6-dihydroxytoluene, pyrogallol, 1,1,3-tris(hydroxyphenyl)propane, bis(4-hydroxyphenyl)methane, 2,2-bis(4-hydroxyphenyl)propane, bis(4-hydroxyphenyl)sulfone and 4,4'-dihydroxybiphenyl as well as novolaks of formaldehyde or acetaldehyde and phenol, chlorophenol or alkylphenols containing up to 9 carbon atoms in the alkyl moiety, in particular cresol and phenol novolaks.

Preferred hardeners are polycarboxylic acid anhydrides such as tetrahydrophthalic anhydride, hexahydrophthalic anhydride and methyltetrahydrophthalic anhydride, as well as aromatic polyamines, in particular bis(4-aminophenyl)methane, bis(4-aminophenyl)sulfone and m- or p-phenylenediamine.

The hardeners (b) are employed in the amounts conventionally used in the art of epoxy resins, and conveniently in such amounts that about 0.7 to 1.5 equivalents of functional groups of the hardener (b) are present per one epoxide equivalent.

The mixtures of this invention may also contain further customary additives, in particular (c) accelerators or curing catalysts and/or (d) further epoxy resins.

Compounds which are known per se may also be employed as accelerators (c), e.g.: complexes of amines, in particular tertiary amines such as monoethylamine, trimethylamine and octyldimethylamine, with boron trifluoride or boron trichloride, tertiary amines such as benzyldimethylamine, tris(dimethylaminomethyl)phenol, hexamethylene tetramine or 1,6-bis(dimethylamino)hexane; urea derivatives such as N-4-chlorophenyl-N',N'-dimethylurea (monuron), N-3-chloro-4-methylphenyl-N',N'-dimethylurea (chlortoluron), N-(2-hydroxyphenyl)-N',N'-dimethylurea and N-(2-hydroxy-4-nitrophenyl)-N',N'-dimethylurea, and unsubstituted or substituted imidazoles such as imidazole, benzimidazole, 1-methylimidazole, 2-ethyl-4-methylimidazole, 2-vinylimidazole, 2-phenylimidazole, 2-phenyl-4-methylimidazole, 1-(2,6-dichlorobenzoyl)-2-phenylimidazole and 1-(2,4,6-trimethylbenzoyl)-2-phenylimidazole.

Tertiary amines, in particular benzyldimethylamine, and imidazoles, in particular 2-phenylimidazole, 3-methylimidazole and 2-ethyl-4-methylimidazole, are preferred accelerators (c).

Suitable epoxy resins (d) are preferably those containing on average more than one group of formula III

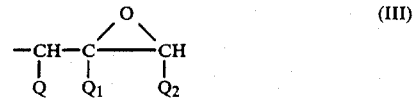

wherein each of Q and $Q_2$ is a hydrogen atom and $Q_1$ is a hydrogen atom or a methyl group or Q and $Q_2$ together are —CH$_2$CH$_2$— or —CH$_2$—CH$_2$—CH$_2$— and $Q_1$ is a hydrogen atom, which group is attached to a hetero atom, e.g. a sulfur atom and, preferably, to an oxygen or nitrogen atom.

Typical examples of such resins are polyglycidyl esters and poly(β-methylglycidyl)esters which are derived from aliphatic, cycloaliphatic or aromatic polycarboxylic acids. Examples of suitable polycarboxylic acids are: succinic acid, glutaric acid, adipic acid, pimelic acid, suberic acid, azelaic acid, sebacic acid, dimerised or trimerised linoleic acid, tetrahydrophthalic acid, 4-methyltetrahydrophthalic acid, hexahydrophthalic acid, 4-methylhexahydrophthalic acid, phthalic acid, isophthalic acid and terephthalic acid.

Further examples are polyglycidyl ethers and poly(β-methylglycidyl)ethers which are obtained by reacting a compound containing at least two alcoholic and/or phenolic hydroxyl groups per molecule with epichlorohydrin or with allyl chloride, and then epoxidising the reaction product with a peracid.

Examples of suitable polyols are: ethylene glycol, diethylene glycol, poly(oxyethylene)glycols, propane-1,2-diol, poly(oxypropylene)glycols, propane-1,3-diol, butane-1,4-diol, poly(oxytetramethylene)glycols, pentane-1,5-diol, hexane-2,4,6-triol, glycerol, 1,1,1-trimethylolpropane, pentaerythritol and sorbitol; 1,3- and 1,4-cyclohexanediol, bis(4-hydroxycyclohexyl)methane, 2,2-bis(4-hydroxycyclohexyl)propane and 1,1-bis(hydroxymethyl)cyclohex-3-ene; N,N-bis(2-hydroxyethyl)aniline and 4,4'-bis(2-hydroxyethylamino)diphenylmethane; resorcinol, hydroquinone, bis(4-hydroxyphenyl)methane (bisphenol F), 2,2-bis(4-hydroxyphenyl)propane (bisphenol A), 2,2-bis(4-hydroxy-3,5-dibromophenyl)propane (tetrabromobisphenol A), 1,1,2,2-tetrakis(4-hydroxyphenyl)ethane, 4,4'-dihydroxybiphenyl, bis(4-hydroxyphenyl)sulfone, as well as novolaks of formaldehyde or acetaldehyde and phenol, chlorophenol or alkylphenols containing up to 9 carbon atoms in the alkyl moiety, preferably cresol and phenol novolaks.

Suitable poly(N-glycidyl) compounds are products obtained by dehydrochlorination of reaction products of epichlorohydrin and amines containing at least two active hydrogen atoms bonded to amino nitrogen atoms. Examples of suitable amines are: aniline, n-butylamine, bis(4-aminophenyl)methane, 1,3- and 1,4-xylylenediamine, 1,3- and 1,4-bis(aminomethyl)cyclohexane and bis(4-methylaminophenyl)methane. Further suitable compounds are: triglycidyl isocyanurate, N,N'-diglycidyl derivatives of cyclic alkylene ureas such as ethylene urea and 1,3-propylene urea, or hydantoins such as 5,5-dimethylhydantoin.

Examples of poly(S-glycidyl) compounds are the di-S-glycidyl derivatives of dithiols such as ethanol-1,2-dithiol and bis(4-mercaptomethylphenyl)ether.

Examples of epoxy resins containing one or more groups of the formula III, wherein Q and $Q_2$ together are a —$CH_2CH_2$— or —$CH_2CH_2CH_2$— group are bis(2,3-epoxycyclopentyl)ether, 2,3-epoxycyclopentyl glycidyl ether, 1,2-bis(2,3-epoxycyclopentyloxy)ethane, 3,4-epoxy-6-methylcyclohexylmethyl-3',4'-epoxy-6'-methylcyclohexane carboxylate and 2-(3,4-epoxy)cyclohexyl-5,5-spiro(3',4'-epoxy)cyclohexane dioxane.

Also eligible are epoxy resins in which the epoxy groups are attached to hereto atoms of different kind, or in which some or all of the epoxy groups are central, for example the N,N,O-triglycidyl derivative of 4-aminophenol, N-glycidyl-N'-(2-glycidyloxypropyl)-5,5-dimethylhydantoin, vinylcyclohexene dioxide, limonene dioxide and dicyclopentadiene dioxide.

As component (d) it is particularly preferred to use diglycidyl ethers or advanced diglycidyl ethers of dihydric phenols, in particular diglycidyl ethers or advanced diglycidyl ethers of 2,2-bis(4-hydroxyphenyl)propane, 2,2-bis(3,5-dibromo-4-hydroxyphenyl)propane, bis(4-hydroxyphenyl)methane, bis(4-hydroxycyclohexyl)methane or 2,2-bis(4-hydroxycyclohexyl)propane; polyglycidyl ethers of novolaks, or tetraglycidylated 4,4'-diaminodiphenylmethane. Most preferred are diglycidyl ethers or advanced diglycidyl ethers of bisphenol A, tetrabromobisphenol A or bisphenol F, polyglycidyl ethers of phenol/formaldehyde or cresol/formaldehyde novolaks, or mixtures thereof.

When using higher proportions of epoxy resins (d), e.g. in amounts of up to 90% by weight, based on the components (a) and (d), the compounds of formula I may also be employed as reactive diluents.

The components (b) and (c) are employed in the customary effective amounts, i.e. in amounts sufficient for the curing of the mixtures of the invention. The ratio of the components (a), (b), (c) and, if present, (d) is dependent on the nature of the compounds employed, the required curing rate and the properties desired in the final product and can readily be determined by the person skilled in the art of epoxy resin curing. If the hardener (b) is an amine, then normally 0.75 to 1.25 equivalents of active hydrogen bonded to the amino nitrogen atoms are employed per epoxide equivalent. In the case of polycarboxylic acid or polycarboxylic acid anhydride hardeners, usually 0.4 to 1.1 equivalents of carboxyl or anhydride groups are employed per epoxide equivalent. If polyphenols are used as hardeners, then it is convenient to employ 0.75 to 1.25 phenolic hydroxyl groups per epoxide equivalent. Accelerators (c) are generally used in amounts of 0.1 to 5% by weight, based on the epoxy resins (a) and, if present, (d).

If desired, (further) reactive diluents may be added to the curable mixtures in order to reduce the viscosity. Examples of such reactive diluents are styrene oxide, butyl glycidyl ether, 2,2,4-trimethylpentyl glycidyl ether, phenyl glycidyl ether, cresyl glycidyl ether or glycidyl esters of synthetic, highly branched, mainly tertiary, aliphatic monocarboxylic acids. The mixtures of this invention may also contain, as further customary additives, plasticisers, extenders, fillers and reinforcing agents such as bituminous coal tar, bitumen, textile fibres, glass fibres, asbestos fibres, boron fibres, carbon fibres, mineral silicates, mica, quartz powder, aluminium oxide hydrate, betonites, kaolin, silica aerogel or metal powders, e.g. aluminium powder or iron powder, and also pigments and dyes such as carbon black, oxide pigments and titanium dioxide, flame retardants, thixotropic agents, flow control agents such as silicones, waxes and stearates (some of which are also employed as mould release agents), and adhesion promoters, antioxidants and light stabilisers.

The mixtures of this invention are employed e.g. as adhesives or in surface protection. However, said mixtures are employed in particular for the preparation of cured products for application in the electrical and, especially, electronics industries. The mixtures may be employed in a formulation adapted to the respective special field of application, in an unfilled or filled state, e.g. as coating compositions, varnishes, compression moulding compositions, dipping resins, casting resins, impregnating resins, laminating resins and adhesives.

The curing of the mixtures of this invention can be carried out in a manner known per se in one or two steps. The curing of the mixtures of this invention is generally effected by heating to temperatures in the range from 80° to 200° C., in particular from 100° to 180° C.

The cured products prepared with the compounds of formula I of this invention are characterised by good mechanical, thermal and chemical properties, e.g. good shear strength, a high heat deflection temperature and good chemical stability.

The invention is illustrated in more detail by the following Examples.

A. Preparation of the starting material (4-Allyl-2,6-dimethylphenyl glycidyl ether)

In a glass reaction vessel equipped with metering means, stirrer, thermometer and an azeotropic distillation head fitted with reflux condenser and vacuum attachment, 350 g (1 mole) of 4-allyl-2,6-dimethylphenol, 1796 g (19.42 moles) of epichlorohydrin and 16.20 g of tetramethylammonium chloride are mixed together, and the resultant mixture is heated to 60° C. and then stirred for 2 hours at 60° C. By applying a vacuum of 6700 Pa, the epichlorohydrin is brought to reflux at the reaction temperature (about 60° C.). In the course of 3.5 hours, 190 g of a 50% aqueous NaOH solution are added dropwise, the temperature of the reaction mixture being held at 60° C. During the reaction, the water formed is distilled off with the boiling epichlorohydrin. After the addition of the NaOH solution, the reaction mixture is stirred for about a further 2 hours. When the reaction is complete, the sodium chloride formed is filtered off, and the filtrate is neutralised with 1 liter of 10% Na₂SO₄ solution. The organic phase is separated and washed with two 600 ml portions of distilled water, separated from the aqueous phase and dried over sodium sulfate. Subsequently, the excess epichlorohydrin is distilled off at 60° C./2660 Pa by means of a rotary evaporator. Distillation of the residue at 110° C./1.3 Pa affords 358 g (75.5% of theory) of 4-allyl-2,6-dimethylphenyl glycidyl ether; epoxide content 4.54 equivalents/kg.

Elementary analysis: calculated: C 76.68%; H 8.73%; found: C 76.52%; H 8.43%

¹H-NMR spectrum: 2.2 ppm (s) 6H (CH₃), ca. 2.75 ppm (m) 2H

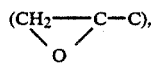

ca. 3.3 ppm (m) 3H

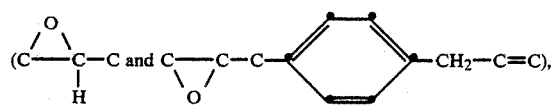

ca. 3.85 ppm (m) 2H

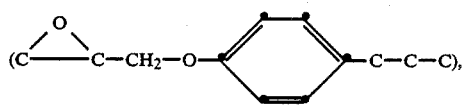

5.1 ppm (m) 2H (CH₂=C—C), 6.0 ppm (m) 1H

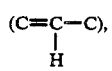

6.85 ppm (m) 2H

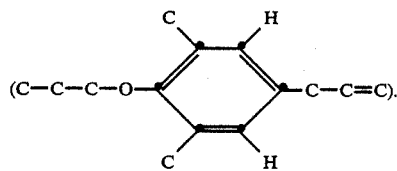

B. Preparatory Examples

Example 1

A 350 ml sulfurating flask equipped with thermometer, stirrer, cooler and drip funnel is charged with 46.30 g (0.21 mole) of 4-allyl-2,6-dimethylphenyl glycidyl ether, 1.93 g of sodium acetate and 160 ml of chloroform, and the batch is heated to 35°–40° C. At this temperature, 52.3 g (0.28 mole) of 40% peracetic acid are then added dropwise over about 1 hour. The reaction mixture is then held at this temperature for a further 4 hours until the educt is no longer discernible in the gas chromatograph. When the reaction is complete, the reaction mixture is diluted in chloroform and the resultant solution is washed with 3% NaOH until neutral, made peroxide-free with sodium sulfite, dried over sodium sulfate and filtered. The filtrate is concentrated by rotary evaporation, affording 47.6 g of 4-(2,3-epoxypropyl)-2,6-dimethylphenyl glycidyl ether in the form of a low viscous oil; epoxide content 8.1 equivalents/kg (95.13% of theory).

¹H-NMR spectrum: 2.25 ppm (s) 6H (CH₃), 2.5–3.0 ppm (m) 6H

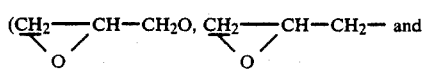

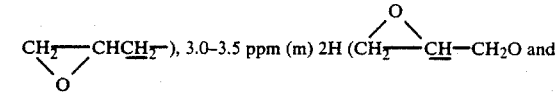

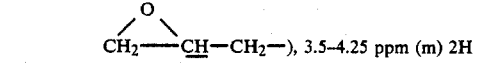

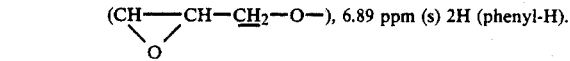

Example 2

A 350 ml sulfurating flask equipped with thermometer, stirrer, cooler and drip funnel is charged with 21.8 g (0.10 mole) of 4-allyl-2,6-dimethylphenyl glycidyl ether, 10.9 g (0.24 mole) of formic acid and 135 ml of chloroform. At room temperature, 23.2 g (0.47 mole) of hydrogen peroxide are then added dropise over 4 hours. The reaction miture is held at this temperature overnight. It is subsequently taken up in chloroform and the resultant solution is washed twice with 3% NaOH solution until neutral, made peroxide-free with sodium sulfite, dried over sodium sulfate and filtered. The filtrate is concentrated, affording 20.03 g (80.50% of theory) of 4-(2,3-epoxypropyl)-2,6-dimethylphenyl glycidyl ether in the form of a low viscous resin; epoxide content 7.7 equivalents/kg (90.11% of theory).

Example 3

4-(2,3-Epoxypropyl)-2,6-dichlorophenyl glycidyl ether

A 100 ml sulfurating flask equipped with stirrer, cooler, thermometer and drip funnel is charged with 13.0 g (0.05 mole) of 4-allyl-2,6-dichlorophenyl glycidyl ether in 40 ml of toluene and 0.5 g of sodium acetate. Over 2 hours, 14.0 g (0.07 mole) of 10% peracetic acid are then added dropwise at 30°–50° C. After the dropwise addition, the reaction mixture is diluted with 300 ml of toluene, the resultant aqueous phase is separated and the organic phase is washed with two 150 ml portions of NaHCO₃ (5%) and then washed with 150 ml of water. The organic phase is dried over sodium sulfate and made peroxide-free with sodium sulfite and filtered. The filtrate is concentrated, affording 12.7 g (92.3%) of a pale yellow resin with an epoxide content of 5.62 eq/kg (77.75%) and a viscosity of 280 mPas/25° C.

Example 4

4-(2,3-Epoxypropyl)-2,6-diphenylphenyl glycidyl ether

A 100 ml sulfurating flask equipped with stirrer, cooler, thermometer and drip funnel is charged with 13.7 g (0.04 mole) of 4-allyl-2,6-diphenylphenyl glycidyl ether in 20 ml of toluene and 0.7 g of sodium acetate. Over 2 hours, 9.13 g (0.048 mole) of 40% peracetic acid are added at a temperature in the range from 30° to 50° C. When the dropwise addition is complete, the reaction mixture is stirred for a further 7 hours. When the reaction is complete, the reaction mixture is diluted with 700 ml of toluene, the resultant aqueous phase is separated and the organic phase is washed with two 150 ml portions of NaHCO$_3$ (5%) and then washed with 150 ml of water. The organic phase is dried over Na$_2$SO$_4$ and made peroxide-free with Na$_2$SO$_3$ and filtered. The filtrate is concentrated, affording 12.46 g (86.5%) of a yellow resin with an epoxide content of 4.99 eq/kg (89.5%) and a viscosity of 6850 mPas/40° C.

C. Application Examples

Examples I and II

The following components are processed to curable mixtures A and B (parts are by weight):

|  | Mixture A | Mixture B |
|---|---|---|
| 4-(2,3-epoxypropyl)-2,6-di- methylphenyl glycidyl ether | 100 | 100 |
| 4,4'-diaminodiphenylmethane (hardener) | 39.6 | — |
| hexahydrophthalic anhydride (hardener) | — | 104.5 |
| 3-methylimidazole (accelerator) | — | 0.5 |

The reactivity[1] and viscosities of these mixtures are determined. The results are shown in the following Table I.

(1) determined by means of the gel times

TABLE I

|  |  | Example | |
|---|---|---|---|
|  |  | I (Mixture A) | II (Mixture B) |
| gel times at | 100° C. min/sec | n.d. | 100' |
|  | 120° C. | 50' | 26' |
|  | 140° C. | 25'15" | 8'13" |
|  | 160° C. | 12'47" | 3' |
|  | 180° C. | 5'43" | 1'21" |
| viscosity η at 80° C.: |  |  |  |
| initial viscosity mPas |  | 15 | 10 |
| viscosity doubled after min |  | about 110 | 80 | n.d. = not determined

Examples III–VI

The mixtures A and B described in Examples I and II are processed to moulded articles or films and
(1) cured for 4 hours at 100° C. and for 8 hours at 140° C. or
(2) cured for 6 hours at 180° C.

The following properties of the cured moulded articles and films are determined:
the glass transition temperature T$_g$:
  determined by differential scanning calorimetry (DSC)
  determined by thermomechanical analysis (TMA)
the shear strength according to DIN 53 283
the chemical stability and the resistance to friction according to DIN 53 230 (tests carried out on films)

The results are shown in the following Table II.

TABLE II

|  | Example | | | |
|---|---|---|---|---|
|  | III (Mixture A) | IV (Mixture B) | V (Mixture A) | VI (Mixture B) |
| curing at | 4 h/100° C. + 8 h/140° C. | | 6 h/180° C. | |
| T$_g$ determined by DSC °C. | 163 | 120 | 177 | 130 |
| determined by TMA °C. | 159 | 118 | 168 | 119 |
| shear strength according to DIN 53 283[1] N/mm$^2$ | 9.3 | 13.1 | 10.3 | 15.7 |
| chemical stability according to DIN 53 230: | | | | |
| in distilled water | 0 | n.d. | 0 | n.d. |
| in 5N NaOH | 0 | n.d. | 0 | n.d. |
| in 5N H$_2$SO$_4$ | 0 | n.d. | 0 | n.d. |
| friction test according to DIN 53 230 (20 rubbings) | | | | |
| in acetone | 0 | n.d. | 0 | n.d. |
| in chlorobenzene[2] | 0 | n.d. | 0 | n.d. |

[1]Average of 10 measurements
[2]The value 0 indicates that after rubbing the film in a to-and-fro motion 20 times with a cotton swab impregnated with one of the above-mentioned solvents, no change in the surface of said film is observed.
n.d. = not determined

What is claimed is:

1. A compound of the formula

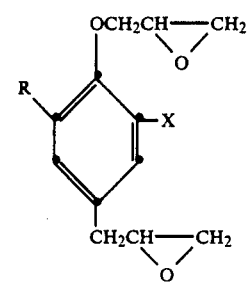

wherein X is a group R' or X is a group of the formula

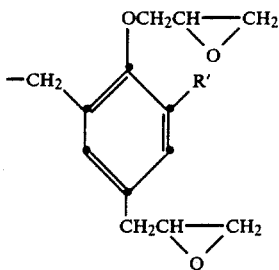

and each of R and R' independently of the other is alkyl of 1 to 4 carbon atoms, alkoxy of 1 to 2 carbon atoms, a halogen atom or phenyl.

2. A compound according to claim 1 wherein R and R' have the same meaning.

3. A compound according to claim 1 wherein X is R'.

4. A compound according to claim 1 wherein X is R', and wherein each of R and R' is methyl, tert-butyl, methoxy, chlorine or phenyl.

5. A compound according to claim 1 wherein X is R', and each of R and R' is methyl.

6. A curable composition which comprises
 (a) a compound according to claim 1, and
 (b) an effective amount of a hardener for component (a).

7. A composition according to claim 6 which additionally contains (c) an effective amount of a curing accelerator.

8. A composition according to claim 6 which additionally contains (d) a further epoxy resin.

9. A composition according to claim 7 which additionally contains (d) a further epoxy resin.

10. A method of bonding two surfaces which comprises
 (a) applying a composition according to claim 6 as an adhesive layer to at least one of the surfaces, and
 (b) bringing said surface into contact with the second surface.

* * * * *